United States Patent [19]

Bagga et al.

[11] 4,175,173
[45] Nov. 20, 1979

[54] POWDER COATING COMPOSITIONS CONTAINING AN EPOXIDE RESIN AND AN ACID HARDENER

[75] Inventors: Madan M. Bagga, Cambridge; Noel S. Moss, Duxford, both of England

[73] Assignee: Ciba-Geigy Corporation, Ardsley, N.Y.

[21] Appl. No.: 940,678

[22] Filed: Sep. 8, 1978

[30] Foreign Application Priority Data

Sep. 9, 1977 [GB] United Kingdom ............... 37685/77

[51] Int. Cl.$^2$ ............................................. C08G 59/42
[52] U.S. Cl. ..................................... 528/97; 427/195; 428/413; 428/418; 528/98; 528/100; 528/104; 528/112
[58] Field of Search ................... 528/98, 97, 100, 112, 528/104

[56] References Cited

U.S. PATENT DOCUMENTS

| | | | |
|---|---|---|---|
| 3,239,537 | 3/1966 | Steckler et al. | 260/346.3 |
| 4,101,518 | 7/1978 | Takamori et al. | 528/100 |

*Primary Examiner*—Earl A. Nielsen
*Attorney, Agent, or Firm*—Joseph F. DiPrima

[57] ABSTRACT

Powder coating compositions comprise an epoxide resin and a carboxylic acid of formula

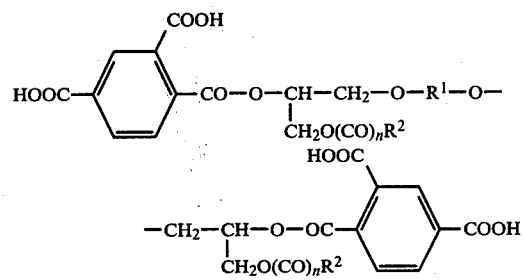

where
$R^1$ represents a phenylene or naphthylene group or a group comprising 2 or 3 phenylene radicals linked by one or two carbon-carbon bonds, ether oxygen atoms, sulfur atoms, or sulfonyl, sulfoxide, carbonyl or alkylene groups,
$R^2$ represents a saturated alkyl group, a benzenoid group or an aralkyl group, and
both n are the same and represent zero or 1.

10 Claims, No Drawings

POWDER COATING COMPOSITIONS CONTAINING AN EPOXIDE RESIN AND AN ACID HARDENER

BACKGROUND TO THE INVENTION

This invention relates to curable compositions comprising an epoxide resin and an acid containing four carboxyl groups, particularly powder coating compositions, and to the use of such compositions.

Techniques for coating articles with a plastics material in powder form are well known. A typical method is fluidised bed powder coating, in which a preheated article is dipped briefly into a fusible plastics powder which is kept in a fluidised state by an ascending current of gas. On contact with the hot article, the powder melts and clings to the surface and, if it is thermosettable, may be so cured. Another widely used method is electrostatic powder coating. In this method the object to be coated is earthed, and the coating particles are given an electrostatic charge and are projected onto the earthed object. Once the object has been coated, it is heated to fuse the coating and, when a thermosettable resin is used, to cure the resin.

Formulation of fusible, thermosettable powder coating compositions requires a material of sufficiently high softening point that it may be milled to a free-flowing powder. At the same time, it is highly desirable that the composition melts initially and then cures at a relatively low temperature, in order that the article to be coated does not have to be heated to a very high temperature. The choice of curing agent is therefore somewhat restricted, if compliance with these criteria is to be achieved.

A particularly successful curing agent for epoxide resins is trimellitic anhydride (benzene-1,2,4-tricarboxylic acid 1,2-anhydride), fulfilling the requirements given above. It is, however, unpleasant to handle in the finely powdered state, being irritant to the skin and mucous membranes. It is also hygroscopic, and special precautions must be taken to exclude water during the milling of this anhydride if its partial conversion into trimellitic acid is to be avoided.

Attempts have been made to overcome these difficulties by reaction of the acid or the anhydride group of trimellitic anhydride with certain diols or polyols. Such attempts have been only partially successful. In British patent specifications Nos. 963,557, 1,019,568, and 1,318,926, for example, such materials are described but they suffer from some of the drawbacks of trimellitic anhydride itself. Some are sensitive to moisture whilst others form only sticky solids which cannot readily be converted into free-flowing powders. Others have a high melting point, which prevents them from forming smooth coatings unless heated to a very high temperature.

There is therefore a need for curing agents, suitable for use in epoxide resin powder coating compositions, which have the desired softening properties, are neither hygroscopic nor irritant when powdered, and which cure the resin to give a hard, glossy finish.

DETAILED DISCLOSURE

We have now found that these objects may be achieved if there is used, as the curing agent in an epoxide resin powder coating composition, a carboxylic acid of the formula

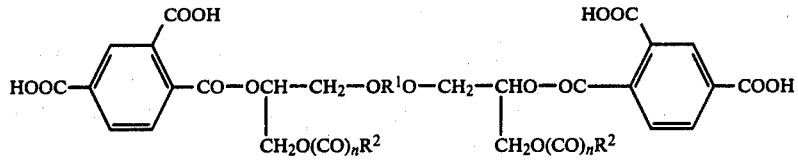

where
$R^1$ represents a phenylene or naphthylene group, or a group comprising two or three phenylene radicals linked by one or two carbon-carbon bonds, one or two ether oxygen atoms, one or two sulfur atoms, or by one or two sulfonyl, sulfoxide, carbonyl, or alkylene groups of 1 to 6 carbon atoms, and either both n represent zero, in which case $R^2$ represents a saturated alkyl group of 1 to 16 carbon atoms, a benzenoid group of 6 to 12 carbon atoms or an aralkyl group of 7 to 16 carbon atoms, or both n represent 1, in which case $R^2$ represents a saturated alkyl group of 1 to 3 carbon atoms, a benzenoid group of 6 to 12 carbon atoms, or an aralkyl group of 7 to 16 carbon atoms.

Preferably the alkyl groups are of 1 to 12 carbon atoms, such as n-butyl groups, the benzenoid groups are phenyl groups which may be substituted by up to three alkyl groups of 1 to 9 carbon atoms or by up to three halogen atoms, particularly chlorine atoms, such as phenyl, p-cresyl, p-butylphenyl, p-octylphenyl, and p-nonylphenyl groups, and the aralkyl groups are phenylalkyl groups. Especially preferred groups $R^2$ are, when n represents zero, an alkyl group of 4 to 9 carbon atoms, an unsubstituted phenyl group, and a benzyl group and, when n represents one, an alkyl group of 1 to 3 carbon atoms., or a phenyl group.

Preferred organic radicals $R^1$ are m-phenylene, p-phenylene, and groups of formula

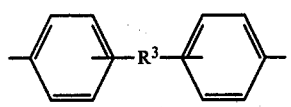

where $R^3$ represents a carbon-carbon bond, an oxygen or sulfur atom, a group of formula —$SO_2$—, or —CO—, or an alkylene group of 1 to 6 carbon atoms. Compounds in which $R^3$ represents an isopropylidene,

or a methylene group are particularly preferred. Specific preferred tetracarboxylic acids are 2,2-bis(p-(2-(2,4-dicarboxyphenylcarbonyloxy)-3-phenoxypropyl)-phenyl)propane, 2,2-bis(p-(2-(2,4-dicarboxyphenylcarbonyloxy)3-butoxypropyl)phenyl)propane, bis(p-(2-(2,4-dicarboxyphenylcarbonyloxy)3-butoxypropyl)- phenyl)methane, 2,2-bis(p-(2-(2,4-dicarboxyphenylcarbonyloxy)-3-(methylcarbonyloxy)propyl)phenyl)propane, 2,2-bis(p-(2-(2,4-dicarboxyphenylcarbonyloxy)-3-(benzoyloxy)propyl)phenyl)propane, 2,2-bis(p-(2-(2,4-dicarboxyphenylcarbonyloxy)-3-(ethylcarbonyloxy)propyl)phenyl)propane, 2,2-bis(p-(2-(2,4-dicarboxyphenylcarbonyloxy)-3-benzyloxypropyl)phenyl)propane, and 1,3-bis(2-(2,4-dicarboxyphenylcarbonyloxy)-3-phenoxypropyloxy)benzene.

The carboxylic acids of formula I are very stable on storage and are substantially non-reactive towards epoxide resins at normal room temperatures. A powdered mixture of an acid of formula I and an epoxide resin may therefore be stored at room temperature for many months without deterioration but cures rapidly when heated above 120° C. Such mixtures are ideally suited for use as powder coatings.

This invention therefore provides a solid, curable composition in powder form comprising an epoxide resin and a carboxylic acid of formula I. The amount of acid of formula I present in such compositions is preferably from 10 to 30 parts per 100 parts by weight of the epoxide resin. Such compositions may further contain, calculated on the weight of the total composition, up to 2% of a flow control agent such as a poly(butyl acrylate), up to 50% of a pigment such as titanium dioxide, up to 50% of an inert filler such as talc or barytes, up to 0.25% of an accelerator for the curing reaction, such as an imidazole (e.g., 2-methylimidazole) or lead naphthenate, up to 10% of a plasticizer, such as a poly(caprolactone), dimethyl terephthalate or dibutyl phthalate, and, calculated on the weight of the epoxide resin, up to 20% of a second hardener which is an acid or acid anhydride, such as pyromellitic acid anhydride, an acid-functional polyester, and glycerol trimellitate (i.e., 1,3-bis(2,4-dicarboxybenzoyloxy)propan-2-ol).

The total amount of hardener present should preferably be such as to provide 0.9 to 1.2 carboxyl (including any anhydride) equivalents per epoxide equivalent of the epoxide resin.

The compounds of formula I may be prepared by reaction of a diol of formula III

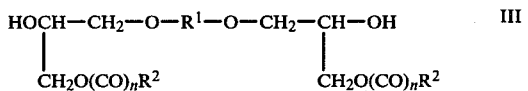

where $R^1$, $R^2$, and n are as hereinbefore defined, with at least two molar equivalents of trimellitic anhydride. This reaction is generally carried out in the absence of a solvent at 120° to 180° C., optionally in the presence of a catalytic amount of a tertiary amine. Heating is continued until the mixture reaches the desired acid value.

The diols of formula III are obtainable by reaction in a known manner of a dihydric phenol of formula $$HO-R^1-OH \qquad IV$$

with two molar equivalents of a monoglycidyl ether or ester of formula

where $R^1$, $R^2$, and n are as hereinbefore defined. This reaction is generally carried out in the absence of a solvent at 100° to 160° C. in the presence of a basic catalyst. Heating is continued until the epoxide group content of the product is substantially zero. Suitable basic catalysts may be organic or inorganic, such as an alkali metal hydroxide or alkoxide, a tertiary amine, or a quaternary ammonium salt.

The diols of formula III in which n represents 1, and those in which n represents zero and $R^2$ represents an aromatic group or an araliphatic group as aforesaid, may also be prepared by reaction of the diglycidyl ether of a dihydric phenol, of formula

with approximately two molar equivalents of a monohydric phenol, an araliphatic alcohol, or a monocarboxylic acid of formula $$R^2(CO)_nOH \qquad VII$$

where $R^1$ and $R^2$ and n are as hereinbefore defined, except that $R^2$ must be an aromatic group or an araliphatic group when n represents zero.

This reaction may be carried out in a known manner, e.g., in the absence of a solvent at 120°–200° C., and usually in the presence of a basic catalyst such as is listed above. Heating is continued until the glycidyl groups are substantially consumed.

Epoxide resins, i.e., materials having, on average, more than one 1,2-epoxide group per molecule, which may be used in the novel compositions include those conventionally used in epoxide resin powder coatings. These resins commonly have an average molecular weight of from 1,000 to 4,000 and more particularly from 1,200 to 2,000.

As examples of such resins may be mentioned polyglycidyl and poly(β-methylglycidyl) esters obtainable by reaction of a compound containing two or more carboxylic acid groups per molecule with epichlorohydrin, glycerol dichlorohydrin, or β-methylepichlorohydrin in the presence of an alkali. Such polyglycidyl esters may be derived from cycloaliphatic polycarboxylic acids such as tetrahydrophthalic acid, 4-methyltetrahydrophthalic acid, hexahydrophthalic acid, and 4-methylhexahydrophthalic acid, and from aromatic polycarboxylic acids such as phthalic acid, isophthalic acid, and terephthalic acid.

Further examples are polyglycidyl and poly(β-methylglycidyl) ethers obtainable by reaction of a compound containing at least two free alcoholic hydroxyl and/or phenolic hydroxyl groups per molecule with the appropriate epichlorohydrin under alkaline conditions or, alternatively, in the presence of an acidic catalyst and subsequent treatment with alkali. These ethers may be made from cycloaliphatic alcohols such as resorcitol, quinitol, bis(4-hydroxycyclohexyl)methane, 2,2-bis(4-hydroxycyclohexyl)propane, and 1,1-bis(hydroxymethyl)cyclohex-3-ene, or from alcohols having aromatic nuclei, such as N,N-bis(2-hydroxyethyl)aniline and bis(p-(2-hydroxyethylamino)phenyl)methane. Or they may be made from mononuclear phenols, such as resorcinol and hydroquinone, and from polynuclear phenols, such as bis(4-hydroxyphenyl)methane, 4,4'-dihydroxydiphenyl, bis(4-hydroxyphenyl)sulfone, 1,1,2,2-tetrakis(4-hydroxyphenyl)ethane, 2,2-bis(4-hydroxyphenyl)propane (otherwise known as bisphenol A), 2,2-bis(3,5-dibromo-4-hydroxyphenyl)propane, and novolaks formed from aldehydes such as formaldehyde, acetaldehyde, chloral, and furfuraldehyde, with phenols such as phenol itself, and phenol substituted in the ring by chlorine atoms or by alkyl groups each containing up to nine carbon atoms, such as 4-chlorophenol, 2-methylphenol, and 4-tert.butylphenol.

poly(N-glycidyl) compounds include, for example, those obtained by dehydrochlorination of the reaction products of epichlorohydrin with amines containing at least two amino-hydrogen atoms, such as bis(4-aminophenyl)methane and bis(4-methylaminophenyl)methane; triglycidyl isocyanurate; and N,N'-diglycidyl derivatives of cyclic alkylene ureas, such as ethyleneurea and 1,3-propyleneurea, and of hydantoins such as 5,5-dimethylhydantoin.

Examples of poly(S-glycidyl) compounds are di-S-glycidyl derivatives of dithiols such as bis(4-mercaptomethylphenyl) ether.

Epoxide resins having the 1,2-epoxide group attached to different kinds of hetero atoms may be employed, e.g., the N,N,O-triglycidyl derivative of 4-aminophenol, the glycidyl ether-glycidyl ester of salicylic acid, N-glycidyl-N'-(2-glycidyloxypropyl)-5,5-dimethylhydantoin, and 2-glycidyloxy-1,3-bis(5,5-dimethyl-1-glycidylhydantoin-3-yl)propane.

The resins employed are preferably solid at room temperature, and may have been advanced if necessary, by reaction with, e.g., a dihydric phenol.

Solid epoxide resins prepared by reaction of an advancing agent, such as bisphenol A, with an epoxide resin obtained by the epoxidation of a cyclic or acyclic polyolefin may also be employed. Typical such epoxidised polyolefins include vinylcyclohexene dioxide, limonene dioxide, dicyclopentadiene dioxide, 3,4-epoxydihydrodicyclopentadienyl glycidyl ether, the bis(3,4-epoxydihydrodicyclopentadienyl)ether of ethylene glycol, 3,4-epoxycyclohexylmethyl 3',4'-epoxycyclohexanecarboxylate and its 6,6'-dimethyl derivative, the bis(3,4-epoxycyclohexanecarboxylate) of ethylene glycol, the acetal formed between 3,4-epoxycyclohexanecarboxyaldehyde and 1,1,-bis-(hydroxymethyl)-3,4-epoxycyclohexane, and epoxidised butadienes or copolymers of butadiene with ethylenic compounds such as styrene and vinyl acetate.

If desired, a mixture of epoxide resins may be used.

Particularly preferred epoxide resins are those having a softening point, measured on a Kofler bench, of from 50° to 140° C., especially those having a softening point of from 65° to 80° C., and a 1,2-epoxide content of at least 0.5 equivalent per kilogram.

Specific preferred resins are advanced polyglycidyl ethers of 2,2-bis(4-hydroxyphenyl)propane or of bis(4-hydroxyphenyl)methane.

The new compositions may be prepared by simple mixing of the ingredients, for example, in a ball mill. An alternative method of preparing them is to melt the ingredients together, preferably in an extruder such as a Buss Ko-Kneader, and then to grind the cooled mass. The compositions preferably have a particle size within the range 0.015 to 500 μm, and especially within the range 10 to 75 μm.

There is further provided a method of coating an article, in which a composition of this invention is applied to the article and heated to a temperature of at least 120° C., preferably between 150° and 220° C., to cure the resin.

This invention is illustrated by the following Examples in which all parts are by weight and temperatures are in degrees Celsius.

The starting materials used in the Examples were prepared as follows:

(a)

2,2-bis(p-(2-Hydroxy-3-phenoxypropyl)phenyl)propane

Method A

Phenyl glycidyl ether (156.6 g), 2,2-bis-(p-hydroxyphenyl)propane (114 g), and benzyltrimethylammonium chloride (2.7 g) were mixed together and heated carefully to 110°, at which temperature an exothermic reaction commenced: the mixture was kept below 130° by cooling. When the exothermic reaction ceased, the mixture was heated at 130° for 2 hours, then at 150° for 3 hours. The resultant product had an epoxy value of only 0.145 equiv./kg, showing that the reaction had proceeded practically to completion.

Method B

Phenyl glycidyl ether (2243.6 g), 2,2-bis(p-hydroxyphenyl)propane (1596 g), and 2-phenylimidazole (0.5 g) were stirred together and heated carefully to 130°, at which temperature a mildly exothermic reaction commenced that kept the reaction at 130°–132° for 40 minutes. The mixture was then heated at 140° for 1 hour and at 180° for 6 hours. The resultant product had an epoxy value of only 0.15 equiv./kg.

Method C

Method B was repeated, but the 2-phenylimidazole was replaced by a 30% solution of sodium methoxide in methanol (0.51 g). The product had an epoxy value of 0.23 equiv./kg.

Method D

Method B was repeated, but the 2-phenylimidazole was replaced by N-benzyldimethylamine (0.5 g) in isopropanol (1 ml). The product had an epoxy value of 0.24 equiv./kg.

(b)

2,2-bis(p-(2-Hydroxy-3-butoxypropyl)phenyl)propane

Butyl glycidyl ether (232.5 g), 2,2-bis(p-hydroxyphenyl)propane (171 g), and benzyltrimethylammonium chloride (4 g) were stirred and heated slowly to 100°. The mixture was kept at 100° for 1 hour, then at 110° for 2 hours, 120° for 1 hour, and 150° for 1½ hours. The product had an epoxy value of 0.2 equiv./kg.

(c) bis(p-(2-Hydroxy-3-butoxypropyl)phenyl)methane bis(p-Hydroxyphenyl)methane (153 g; 67% pure, containing polynuclear homologues), butyl glycidyl ether (232.5 g), and benzyltrimethylammonium chloride (3.85 g) were stirred and heated slowly to 100°, when a mildly exothermic reaction commenced and the temperature rose to 110°. The mixture was kept at 110° for 4½ hours, 120° for 1 hour, and 150° for 1½ hours. The product had an epoxy value of 0.19 equiv./kg.

(d)

2,2-bis(p-(2-Hydroxy-3-methylcarbonyloxypropyl)phenyl)propane 2,2-bis(4-Glycidyloxyphenyl)propane (188.7 g; epoxy value 5.2 equiv./kg), glacial acetic acid (60 g), and 2-phenylimidazole (0.5 g) were stirred together and heated to 120°. The mixture was kept at this temperature for 2 hours, then further heated at 150° for 2 hours. The product had a residual epoxy value of 0.146 equiv./kg.

(e)
2,2-bis(p-(2-Hydroxy-3-benzoyloxypropyl)phenyl)propane 2,2-bis(4-Glycidyloxyphenyl)propane (377.4 g; epoxy value 5.2 equiv./kg), benzoic acid (244 g), and 2-phenylimidazole (0.5 g) were stirred together under nitrogen and heated to 100°. The heating was turned off, and the temperature rose to 112° and remained at this temperature for 30 minutes. When the temperature began to fall, the heating was turned on once more and the mixture was heated to 150° and kept at this temperature for 3 hours. The product had a negligible epoxy content (less than 0.05 equivl./kg.).

(f)
2,2-bis(p-(2-Hydroxy-3-(ethylcarbonyloxy)propyl)-phenyl)propane 2,2-bis(4-Glycidyloxyphenyl)propane (247.2 g; epoxy value 5.5 equiv./kg), propionic acid (111 g), and 2-phenylimidazole (0.35 g) were stirred together under nitrogen and heated to 130°. The mixture was maintained at this temperature for 2 hours, then heated further at 150° for 3 hours. The product had a negligible epoxy content (less than 0.03 equiv./kg).

(g)
2,2-bis(p-(2-Hydroxy-3-benzyloxypropyl)phenyl)propane 2,2-bis(4-Glycidyloxyphenyl)propane (566.1 g; epoxy value 5.2 equiv./kg), benzyl alcohol (324 g), and tetramethylammonium chloride (1.5 g) were stirred under nitrogen at 180° for 7 hours. A further quantity of tetramethylammonium chloride (0.5 g) was added and the mixture was stirred for a further 13 hours at 180°. The product had a negligible epoxy content (only 0.5 equiv./kg.)

(h) 1,3-bis(2-hydroxy-3-phenoxypropyloxy)benzene)

Resorcinol (110 g), phenyl glycidyl ether (329.5 g) and 2-phenylimidazole (0.4 ) were stirred and heated at 130° for 2 hours, then at 150° for 3½ hours. The product had a negligible epoxy content (only 0.2 equiv./kg).

EXAMPLE 1

2,2-bis(p-(2-Hydroxy-3-phenoxypropyl)phenyl)propane (270 g; prepared by method A) was heated to 140° and stirred while trimellitic anhydride (192 g) was added. The mixture was heated at 175° for 4½ hours. The product had an acid value of 250 mg KOH/g (theoretical value for complete esterification is 253 mg KOH/g) and therefore consisted essentially of 2,2-bis(p-(2-(2,4-dicarboxyphenylcarbonyloxy)-3-phenoxypropyl)phenyl)propane. It was a light beige solid, having a Kofler softening point of 75°.

The following materials were mixed:

| "Epoxide resin I" | 303 g |
|---|---|
| poly(butyl acrylate) | 3 g |
| titanium dioxide | 242 g |
| 2,2-bis(p-(2,4-dicarboxyphenyl-carbonyloxy)-3-(phenoxypropyl)phenyl)propane | 100 g |

"Epoxide resin I" denotes an advanced polyglycidyl ether of bisphenol A, having an epoxide equivalent weight of 800, i.e., an average molecular weight of about 1600.

This mixture was extruded through a Buss Ko-Kneader using a barrel temperature of 85°. The molten extrudate was cooled, crushed, and ground to a maximum particle size of 75 μm.

This powder was applied by electrostatic spray to degreased aluminum panels and heated at 200° for 15 minutes, leaving a cured white film 50 μm thick. The gloss was measured by the method described in British Standard No. 3900 Part D2 (1967) using a 60° angle of incidence, and a reverse impact test was carried out according to the method described in British Standard No. 3900 Part E3 (1966).

The experiment was repeated, using starting materials prepared by Methods B, C, and D. The results are given in the Table.

TABLE

| Test | Starting material prepared by Method | | | |
|---|---|---|---|---|
|  | A | B | C | D |
| Gloss | 110% | 110% | 110% | 90% |
| Kofler gel time at 180° | 7¼ mins. | 7¼ mins. | 7 mins. | 7 mins. |
| Time to cure fully at 180° | — | 15 mins. | — | 15 mins. |
| Reverse impact | — | over 4½ mm | over 4½ mm | over 4½ mm |

The coatings prepared from starting materials made by Methods A and C were also tested for chemical resistance. They showed no adverse effects after immersion for two weeks at room temperature in petrol, xylene, ethanol, 2N-acetic acid, water, 2N-sodium hydroxide, 50% sulfuric acid, and various dilute detergents.

EXAMPLE 2

2,2-bis(p-(2-Hydroxy-3-butoxypropyl)phenyl)propane (403 g) was heated to 140°, trimellitic anhydride (288 g) and triethanolamine (0.3 g) were added, and the mixture was heated at 175° for 4 hours. The product had an acid value of 224 mg KOH/g (theoretical value for complete esterification is 243 mg KOH/g), and therefore consisted essentially of 2,2-bis(p-(2-(2,4-dicarboxyphenylcarbonyloxy)-3-butoxypropyl)phenyl)propane. It was a golden-brown solid having a Kofler softening point of 65°.

The following materials were mixed:

| Epoxide resin I | 303 g |
|---|---|
| poly(butyl acrylate) | 3 g |
| titanium dioxide | 242 g |
| 2,2-bis(p-(2-(2,4-dicarboxyphenylcarbonyloxy)-3-butoxypropyl)phenyl)propane | 108 g |

The mixture was converted into a powder and coated onto panels as described in Example 1. The coating was fully cured after heating at 200° for 15 minutes and was smooth and hard, with a gloss of 75%.

EXAMPLE 3 bis(p-(2-Hydroxy-3-butoxypropyl)phenyl)methane (257 g) was heated to 140°, trimellitic anhydride (192 g) and triethanolamine (0.2 g) were added, and the mixture was heated at 175° for 4 hours. The product had an acid value of 240 mg KOH/g and was therefore predominantly bis(p-(2-(2,4-dicarboxyphenylcarbonyloxy)-3-butoxypropyl)phenyl)methane. It was a brown solid, having a Kofler softening point of 61°.

The following materials were mixed, converted into powder, and coated onto panels as described in Example 1:

| | |
|---|---|
| Epoxide resin I | 303 g |
| poly(butyl acrylate) | 3 g |
| titanium dioxide | 242 g |
| bis(p-(2-(2,4-dicarboxyphenylcarbonyloxy) -3-butoxypropyl)phenyl)methane | 104 g |

The coating was fully cured after heating for 15 minutes at 200°, and was smooth and hard, with a gloss of 75%.

EXAMPLE 4

2,2-bis(p-(2-Hydroxy-3-methylcarbonyloxypropyl)-phenyl)propane (198 g) was heated to 150° and stirred while trimellitic anhydride (152.5 g) was added. The mixture was heated at 170° for 2 hours. The product had an acid value of 238 mg KOH/g (theoretical value for complete esterification is 254 mg KOH/g) and therefore consisted essentially of 2,2-bis(p-(2-(2,4-dicarboxy-phenylcarbonyloxy)-3-methylcarbonyloxypropyl)-phenyl)propane. It was a clear, pale straw-coloured solid having a Kofler softening point of 97°.

| | |
|---|---|
| The following materials were mixed: | |
| Epoxide resin I | 303 g |
| poly(butyl acrylate) | 3 g |
| titanium dioxide | 242 g |
| 2,2-bis(p-(2-(2,4-dicarboxyphenylcarbonyloxy) -3-methylcarbonyloxypropyl)phenyl)propane | 93 g |

The mixture was converted into a powder and coated onto panels as described in Example 1. The coating was fully cured after heating at 200° for 15 minutes and was smooth and hard, being resistant to rubbing with a swab soaked in ethyl methyl ketone. Its gloss was 100% and it passed the 3 mm reverse impact test.

EXAMPLES 5–8

Example 4 was repeated, replacing the 2,2-bis(p-hydroxy-3-(methylcarbonyloxypropyl)phenyl)propane by an equimolar amount of the following:
Example 5—2,2-bis(p-(2-hydroxy-3-benzoyloxy-propyl)phenyl)propane
Example 6—2,2-bis(p-(2-hydroxy-3-(ethylcarbonylox-y)propyl)phenyl)propane
Example 7—2,2-bis(p-(2-hydroxy-3-benzyloxypropyl)-phenyl)propane
Example 8—1,3-bis(2-hydroxy-3-phenoxypropyloxy)-benzene.

The acids are blended and tested as described in Example 4, the results being shown in the following Table:

What is claimed is:

1. Solid, curable compositions in powder form, comprising 100 parts by weight of an epoxide resin and 10 to 30 parts by weight of a carboxylic acid of formula

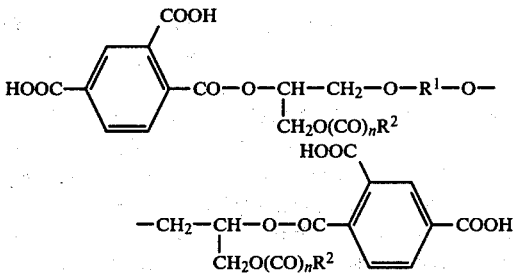

where
$R^1$ represents a phenylene or naphthylene group, or a group comprising two or three phenylene radicals linked by one or two carbon-carbon bonds, one or two ether oxygen atoms, one or two sulfur atoms, or by one or two sulfonyl, sulfoxide, carbonyl, or alkylene groups of 1 to 6 carbon atoms, and
either both n represent zero, in which case $R^2$ represents a saturated alkyl group of 1 to 16 carbon atoms, a benzenoid group of 6 to 12 carbon atoms, or an aralkyl group of 7 to 16 carbon atoms, or
both n represent 1, in which case $R^2$ represents a saturated alkyl group of 1 to 3 carbon atoms, a benzenoid group of 6 to 12 carbon atoms, or an aralkyl group of 7 to 16 carbon atoms.

2. The compositions of claim 1, wherein $R^1$ represents m-phenylene, p-phenylene, or a group of formula

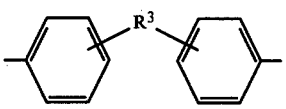

where
$R^3$ represents a carbon-carbon bond, an oxygen or sulfur atom, a group of formula $-SO_2-$, or $-CO-$, or an alkylene group of 1 to 6 carbon atoms.

3. The compositions of claim 1, in which both n represent zero and $R^2$ represents an alkyl group of 1 to 12 carbon atoms, a phenyl group, a phenyl group substituted by up to three alkyl groups of 1 to 9 carbon atoms, a phenyl group substituted by up to three halogen atoms, or a phenylalkyl group.

4. The compositions of claim 1, in which both n represent 1 and $R^2$ represents an alkyl group of 1 to 3 carbon atoms or a phenyl group.

TABLE

| | Soften- ing point ° | Acid | | | Powder coating | | |
|---|---|---|---|---|---|---|---|
| | | Acid value (mg KOH/g) | | Weight used (g) | Reverse impact | Appear- ance | Gloss % |
| Example | | Found | Theory | | | | |
| 5 | 95 | 257 | 236 | 100 | >5 | Smooth, hard | 95 |
| 6 | 85 | 261 | 250 | 95 | >5 | Smooth, hard | 90 |
| 7 | 90 | 249 | 242 | 98 | >5 | Smooth, hard | 100 |
| 8 | 91 | 279 | 272 | 87 | >5 | Smooth, hard | 110 |

5. The compositions of claim 1, in which the carboxylic acid is 2,2-bis(p-(2-(2,4-dicarboxyphenylcarbonyloxy)-3-phenoxypropyl)phenyl)propane, 2,2-bis(p-(2-(2,4-dicarboxyphenylcarbonyloxy)-3-butoxypropyl)phenyl)propane, bis(p-(2-(2,4-dicarboxyphenylcarbonyloxy)-3-butoxypropyl)phenyl)methane, 2,2-bis(p-(2-(2,4-dicarboxyphenylcarbonyloxy)-3-methylcarbonyloxypropyl)phenyl)propane, 2,2-bis(p-(2-(2,4-dicarboxyphenylcarbonyloxy)-3-(benzoyloxy)propyl)phenyl)propane, 2,2-bis(p-(2-(2,4-dicarboxyphenylcarbonyloxy)-3-ethylcarbonyloxypropyl)phenyl)propane, 2,2-bis(p-(2-(2,4-dicarboxyphenylcarbonyloxy)-3-benzyloxypropyl)phenyl)propane, or 1,3-bis(2-(2,4-dicarboxyphenylcarbonyloxy)-3-phenoxypropyloxy)benzene.

6. The compositions of claim 1, in which the epoxide resin has a softening point, as measured on a Kofler bench, of from 50° to 140° C.

7. The compositions of claim 1, in which the epoxide resin has an average molecular weight of from 1000 to 4000 and a 1,2-epoxide content of at least 0.5 equivalent per kilogram.

8. The compositions of claim 1, in which the epoxide resin is an advanced polyglycidyl ether of 2,2-bis(4-hydroxyphenyl)propane or of bis(4-hydroxyphenyl)methane.

9. The compositions of claim 1, having a particle size within the range 0.015 to 500 μm.

10. Articles coated by applying thereto a composition as claimed in claim 1 and heating to a temperature of at least 120° C. to cure the resin.

* * * * *